United States Patent
Cosmescu (10) Patent No.: US 11,395,693 B2
(45) Date of Patent: Jul. 26, 2022

(54) ULTRAPOLAR ELECTROSURGERY BLADE AND PENCIL FOR USE IN ESU MONOPOLAR AND BIPOLAR MODES

(71) Applicant: I.C. Medical, Inc., Phoenix, AZ (US)

(72) Inventor: Ioan Cosmescu, Phoenix, AZ (US)

(73) Assignee: I.C. Medical, Inc., Phoenix, AZ (US)

( * ) Notice: Subject to any disclaimer, the term of this patent is extended or adjusted under 35 U.S.C. 154(b) by 633 days.

(21) Appl. No.: 15/697,335

(22) Filed: Sep. 6, 2017

(65) Prior Publication Data

US 2018/0064486 A1 Mar. 8, 2018

Related U.S. Application Data

(60) Provisional application No. 62/383,855, filed on Sep. 6, 2016.

(51) Int. Cl.
| | |
|---|---|
| *A61B 18/14* | (2006.01) |
| *A61B 18/08* | (2006.01) |
| *A61B 18/00* | (2006.01) |
| *A61B 18/12* | (2006.01) |

(52) U.S. Cl.
CPC ........ *A61B 18/1442* (2013.01); *A61B 18/082* (2013.01); *A61B 18/1402* (2013.01); *A61B 2018/00178* (2013.01); *A61B 2018/00607* (2013.01); *A61B 2018/126* (2013.01); *A61B 2018/1253* (2013.01); *A61B 2018/1422* (2013.01)

(58) Field of Classification Search
CPC .............. A61B 18/1442; A61B 18/082; A61B 18/1402; A61B 2018/1412
See application file for complete search history.

(56) References Cited

U.S. PATENT DOCUMENTS

| | | | |
|---|---|---|---|
| 4,161,950 A | 7/1979 | Doss et al. | |
| 4,248,231 A | 2/1981 | Herczog et al. | |
| 7,727,232 B1* | 6/2010 | Maurer | A61B 18/1402 |
| | | | 606/48 |
| 8,177,783 B2 | 5/2012 | Davison et al. | |
| 8,414,572 B2 | 4/2013 | Davison et al. | |
| 2004/0024396 A1 | 2/2004 | Eggers | |
| 2005/0283151 A1* | 12/2005 | Ebbutt | A61B 18/1402 |
| | | | 606/50 |
| 2007/0005057 A1 | 1/2007 | Heim et al. | |
| 2010/0094283 A1 | 4/2010 | Cosmescu | |
| 2012/0116397 A1 | 5/2012 | Rencher et al. | |
| 2014/0025060 A1* | 1/2014 | Kerr | A61B 18/14 |
| | | | 606/33 |
| 2016/0317209 A1 | 11/2016 | Cosmescu | |

* cited by examiner

*Primary Examiner* — Linda C Dvorak
*Assistant Examiner* — Bo Ouyang
(74) *Attorney, Agent, or Firm* — Zeman-Mullen & Ford, LLP (57) ABSTRACT

An ultrapolar electrosurgery blade and an ultrapolar electrosurgery pencil that can be used in both monopolar and bipolar modes for cutting and coagulating tissue. The ultrapolar electrosurgery blade includes a non-conductive member with opposing planar sides, a cutting end with a sharp cutting edge, and an opposite non-cutting end, an active electrode located on one of the opposing planar sides of the non-conductive member, and a return electrode located on the other opposing planar side of the non-conductive member.

9 Claims, 5 Drawing Sheets

ULTRAPOLAR ELECTROSURGERY BLADE AND PENCIL FOR USE IN ESU MONOPOLAR AND BIPOLAR MODES

CROSS-REFERENCE TO RELATED APPLICATIONS

This application claims priority to provisional patent application having Ser. No. 62/383,855 entitled "Ultrapolar Electrosurgery Blade and Pencil for Use in ESU Monopolar and Bipolar Modes," filed Sep. 6, 2016, which is herein incorporated by reference in its entirety.

FIELD OF INVENTION

The present invention is generally directed to an ultrapolar electrosurgery blade and a ultrapolar electrosurgery pencil for use in both monopolar mode and bipolar mode for cutting and coagulation. The ultrapolar electrosurgery blade has a non-conductive member with opposing planar sides, a cutting end, and an, opposite non-cutting end, an active electrode located on one of the opposing planar sides of the non-conductive member, and a return electrode located on the other opposing planar side of the non-conductive member.

BACKGROUND OF TILE INVENTION

Electrosurgery uses an RF electrosurgical generator (also known as an electrosurgical unit or ESU) and a handpiece with an electrode to provide high frequency, alternating radio frequency (RF) current input at various voltages to cut or coagulate biological tissue. The handpiece may be a monopolar instrument with one electrode or a bipolar instrument with two electrodes. When using a monopolar instrument, a return electrode pad is attached to the patient and the high frequency electrical current flows from the generator, to the monopolar instrument, through the patient to the patient return electrode pad, and back to the generator. Monopolar electrosurgery is commonly used due to its versatility and effectiveness. However, the excessive heat generated with monopolar electrosurgery can cause excessive tissue damage and necrosis of the tissue because the return electrode positioned on the back of the patient causes high voltage and high RF energy to pass through the patient.

In bipolar electrosurgery, active output and patient return functions both occur at the surgery site because both the active and return electrodes are contained in the bipolar instrument. Therefore, the path of the electrical current is confined to the biological tissue located between the active and return electrodes. Although bipolar electrosurgery enables the use of lower voltages and less energy and thereby reduces or eliminates the likelihood of tissue damage and sparking associated with monopolar electrosurgery, it has limited ability to cut and coagulate large bleeding areas.

Accordingly, there is a need for an electrosurgery blade and an electrosurgery pencil that can be used in both monopolar and bipolar modes for cutting and coagulation thereby allowing flexibility for cutting and coagulation of large areas of tissue without the tissue damage when used in monopolar mode and which eliminates passing of energy through the patient when used in bipolar mode. An ultrapolar electrosurgery blade having a sharp cutting end and an active electrode positioned on one opposing planar side of a non-conductive member and a return electrode positioned on the other opposing planar side of the non-conductive member would meet this, need. The ultrapolar electrosurgery blades with a sharp cutting end and an active and return electrode positioned on opposing sides of the electrosurgery blade described with reference to the present invention can be used in both monopolar and bipolar modes thereby providing flexibility to a surgeon or operator. The ultrapolar electrosurgery blades described with reference to the preset invention can be used with an electrosurgery handpiece/pencil that does not have smoke evacuation capability but they are also intended to be used with an electrosurgery pencil/handpiece that is capable of smoke evacuation during the electrosurgery procedure.

SUMMARY OF THE INVENTION

The present invention is directed to an ultrapolar electrosurgery blade which includes a non-conductive planar member having first and second opposite planar sides, a cutting end, and a non-cutting end, an active electrode located on the first opposite planar side wherein at least a portion of the first opposite planar side is exposed near the cutting end of the non-conductive planar member, and a return electrode located on the second opposite planar side wherein at least a portion of the second opposite planar side is exposed near the cutting end of the non-conductive planar member. In one exemplary embodiment of the ultrapolar electrosurgery blade of the present invention, the active electrode located on the first planar side mirrors at least a portion of the return electrode located on the second planar side.

The non-conductive planar member may comprise a ceramic and the active and return electrodes may comprise a stainless steel, a copper, and/or a tungsten. In another exemplary embodiment of the ultrapolar electrosurgery blade of the present invention, the active and return electrodes may each take the form of an elongated conductive layer that extends more than half the length of the non-conductive planar member. At least a portion of the elongated conductive layer of the active electrode may extend to, and along a partial length of, one or more of the opposing, elongated edges of the first opposite planar side and at least a portion of the elongated conductive layer of the return electrode may extend to, and along a partial length of, one or more opposing elongated edges of the second opposite planar side.

In still another exemplary embodiment of the ultrapolar electrosurgery blade of the present invention, the ultrapolar electrosurgery blade includes a non-conductive planar member having first and second opposite planar sides with opposing elongated edges, a cutting end, and an opposite non-cutting end, an active electrode having a rounded or pointed hook-like shaped configuration located on the first opposite planar side of the non-conductive planar member, and a return electrode having a rounded or pointed hook-like shaped configuration located on the second opposite planar side of the non-conductive planar member. The hook-like shaped configuration of the active electrode and the return electrode may be located near the cutting end of the non-conductive planar member without covering at least a portion of the first and second opposite planar sides located near the cutting end of the non-conductive planar member. At least a portion of the hook-like shaped configuration of the active electrode located on the first opposite planar side may mirror at least a portion of the hook-like shaped configuration of the return electrode located on the second opposite planar side of the non-conductive planar member. The non-conductive planar member may comprise a ceramic and the first and second active electrodes and the first and second return electrodes may comprise a stainless steel, a copper, and/or a tungsten.

The cutting end of the non-conductive planar member is a sharp cutting end and may take the form/configuration of a sharp cutting edge with the active and return electrodes located on, opposite planar sides of the non-conductive planar member each lying adjacent to the sharp cutting edge of the non-planar member while still leaving a portion of the non-conductive planar member closest to the sharp cutting edge exposed.

Further, a portion of each of the active and return electrodes may extend to the opposite non-cutting end of the non-conductive planar member. The ultrapolar electrosurgery blade of the present invention may further comprise a first conductive insert member in communication with the active electrode located near the non-cutting end of the non-conductive planar member and a second conductive insert member in communication with the return electrode located near the non-cutting end of the non-conductive planar member. The first and second conductive inserts may each comprise a metal contact member that is made of brass and/or copper.

The ultrapolar electrosurgery blade of the present invention can be used in both monopolar and bipolar modes when used to perform electrosurgery. The conductive insert in communication with the active electrode is connected to a circuit board contained within an electrosurgery pencil for activating the electrosurgery pencil (and the circuit board is in turn connected to an electrosurgery unit generator through an electrical connection means such as a wire) and the conductive insert in communication with the return electrode is connected to the electrosurgery unit generator through an electrical connection means such as wire so that the active and return contacts of the ultrapolar electrosurgery blade are connected to the electrosurgery unit generator. When the ultrapolar electrosurgery blade of the present invention is used in monopolar mode, the monopolar power output mode is selected on the electrosurgical unit generator. When the ultrapolar electrosurgery blade of the present invention is used in bipolar mode, the bipolar power output mode is selected on the electrosurgical unit generator.

The present invention is also directed to an ultrapolar electrosurgery pencil having a handpiece with a first and second, end and an electrosurgery blade positioned in the first end of the handpiece where the electrosurgery blade includes a non-conductive planar member having opposing, planar sides, a cutting end, and an opposite non-cutting end, an active electrode located on one opposing planar side where at least a portion of the opposing planar side is exposed near the non-conductive cutting end of the non-conductive planar member, and a return electrode located on the other opposing planar side where at least a portion of the other opposing planar side is exposed near the non-conductive cutting end of the non-conductive planar member. The handpiece may further comprise a smoke evacuation channel contained therein for evacuating smoke and debris from the surgical site during activation of the electrosurgery pencil, in addition, the handpiece may further comprise only one activation button for coagulation since the sharp cutting end/edge of the nonconductive planar member can make precise cuts without having power applied to the ultrapolar electrosurgery blade. Alternatively, the handpiece may include more than one activation button for cutting and coagulation. The ultrapolar electrosurgery blade may also include a connector which functions to connect the ultrapolar electrosurgery blade to an electrosurgery pencil.

BRIEF DESCRIPTION OF THE DRAWINGS

The subject invention will hereafter be described in conjunction with the appended drawing figures, wherein like numerals denote like elements.

DETAILED DESCRIPTION OF EXEMPLARY EMBODIMENTS

The exemplary embodiments of the ultrapolar electrosurgery blade and pencil for use in electrosurgical unit (ESU) monopolar and bipolar modes of the present invention enable a user or surgeon to perform cutting with the sharp non-conductive tip of the electrosurgery blade as well as coagulation of large areas of biological tissue by using the electrical contacts of the electrosurgery blade. The ultrapolar electrosurgery blade and ultrapolar electrosurgery pencil of the present invention may also perform cutting with the active and return electrodes of the electrosurgery blade. Exemplary embodiments of the ultrapolar electrosurgery blade and the ultrapolar electrosurgery pencil of the present invention include an electrosurgery blade that has a non-conductive member having first and second opposite planar sides and a sharp cutting end, an active electrode positioned on the first opposite planar side of the non-conductive member such that at least a portion of the first opposite planar side is exposed near the cutting end, and a return electrode positioned on the second opposite planar side of the non-conductive member such that at least a portion of the second opposite planar side is exposed near the cutting end. The cutting end of the non-conductive planar member can form a sharp non-conductive cutting end tier cutting biological tissue while the active and return electrodes located on opposite planar side of the non-conductive member can be used to perform coagulation as well as cutting of biological tissue.

Figure 1:
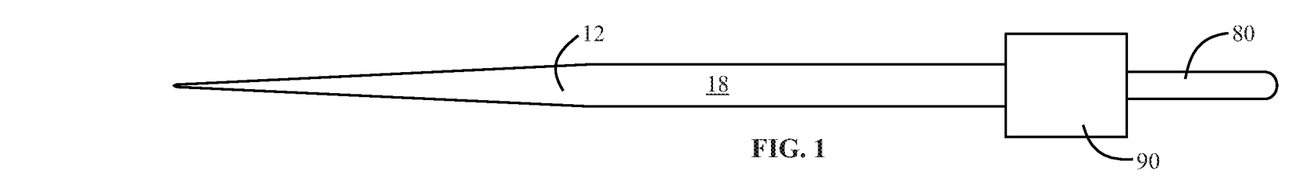
FIG. 1 is a top view of the non-conductive planar member of an exemplary embodiment of the ultrapolar electrosurgery blade of the present invention without the conductive layer but with the conductive inserts for the active and return electrodes.
Figures 2, 3:
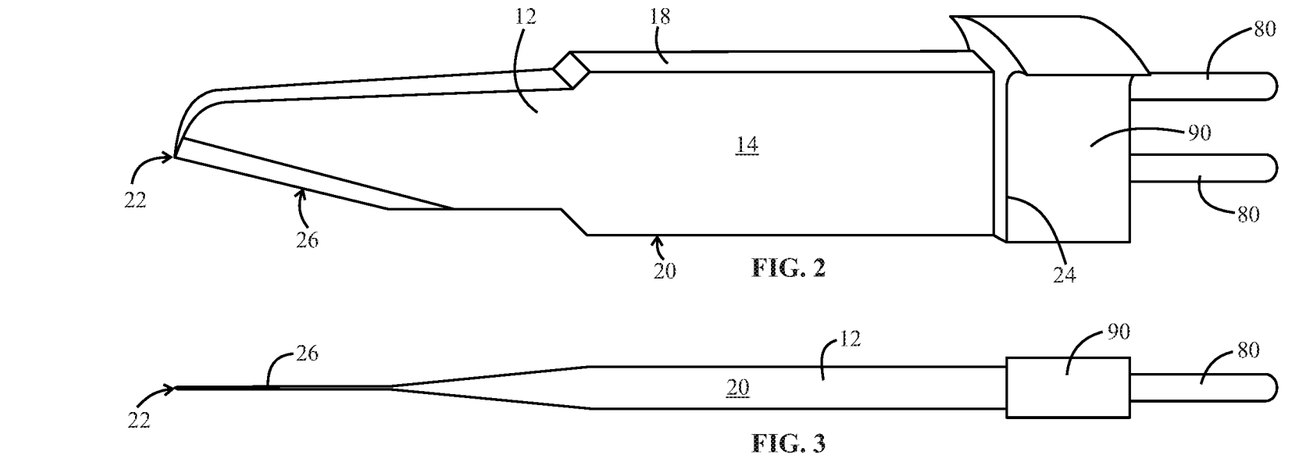
FIG. 2 is a side view of the non-conductive planar member shown in FIG. 1.
FIG. 3 is a bottom view of the non-conductive planar member shown in FIGS. 1 and 2.

FIG. 1 is a top view of the non-conductive member of an exemplary embodiment of the ultrapolar electrosurgery blade of the present invention without the conductive layer but with the conductive inserts for the active and return electrodes. FIG. 2 is a side view of the non-conductive member shown in FIG. 1 and FIG. 3 is a bottom view of the non-conductive member shown in FIGS. 1 and 2. Non-conductive member 12 has first and second opposite planar sides 14, 16, a top 18, a bottom 20, a cutting end 22, and a non-cutting end 24. Cutting end 22 includes a sharp cutting edge 26 located on or near the bottom 20 of non-conductive member 12. The width of non-conductive member 12 is tapered so that the cutting end 22 of non-conductive member 12 has a smaller width than a middle of non-conductive member 12. FIGS. 1-3 also show conductive insert members 80 which are connected to the non-cutting end 24 of the non-conductive member 12 which can be connected to an electrosurgery pencil. The conductive inserts are m communication with the active and return electrodes of the ultrapolar electrosurgery blade (See FIGS. 7-11). The ultrapolar electrosurgery blade of the present invention may also include a connector 90 which ran assist in securing the ultrapolar electrosurgery blade of the present invention within an electrosurgery pencil.

Figure 4:
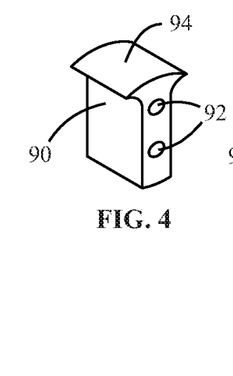
FIGS. 4-6 show views of an exemplary connector which functions to connect the ultrapolar electrosurgery blade to an electrosurgery pencil.
Figures 5, 6:
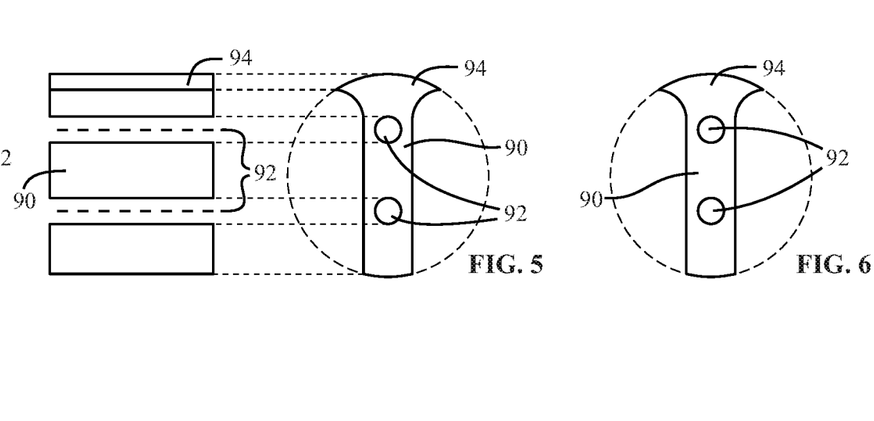

Views of an exemplary connector 90 which functions to connect the ultrapolar electrosurgery blade to an electrosurgical pencil arc shown in FIGS. 4-6. Connector 90 includes two openings 92 into which the conductive insert members 80 can be placed to secure the conductive insert members in relation to the non-conductive planar member 12. Connector 90 also includes at least one rounded portion 94 which lies adjacent to a portion of the interior circumference of an electrosurgical pencil in order to seat the ultrapolar electrosurgery blade within the electrosurgery pencil. The dashed lines in FIG. 6 represent the inner circumference of an electrosurgery pencil. It will be understood by those skilled in the art that connector 90 may form a continuous non-conductive portion of the non-conductive member 12 as shown in FIGS. 7-10.

Figure 7:
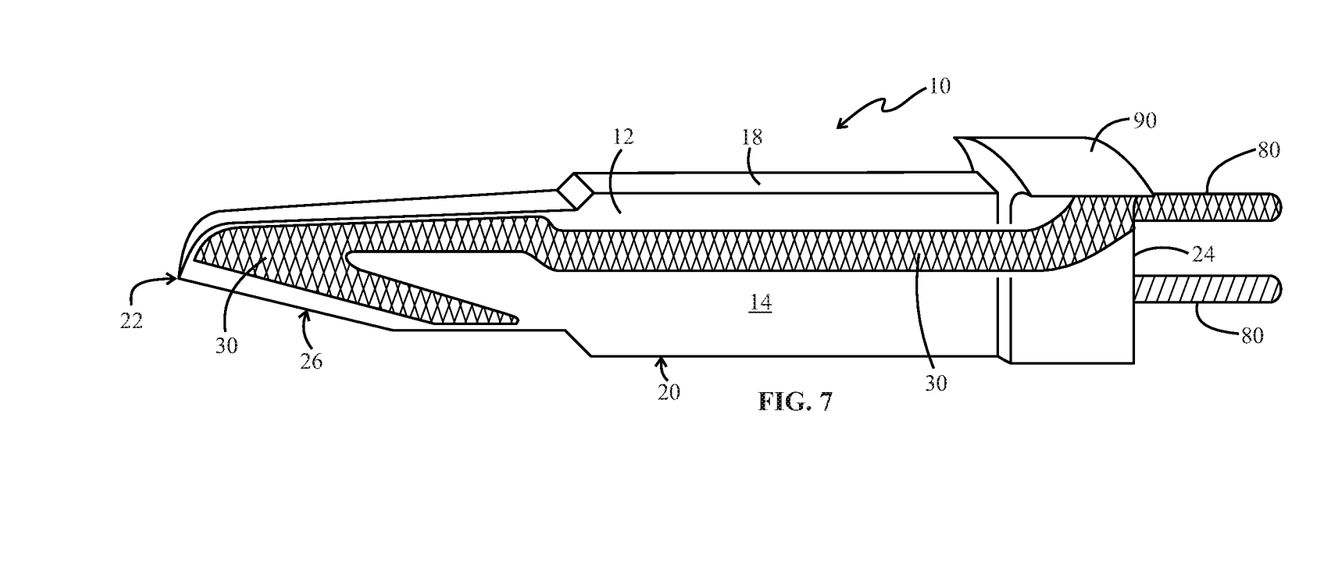
FIG. 7 is a side perspective view of an exemplary embodiment of the ultrapolar electrosurgery blade of the present invention.

FIG. 7 is a side perspective view of an exemplary embodiment of the ultrapolar electrosurgery blade 10 of the present invention which includes non-conductive member 12 having first and second opposite planar sides 14, 16, a top 18, a bottom 20, a cutting end 22 with a sharp cutting edge 26, and a non-cutting end 24, and an active electrode 30 positioned on the first opposite planar side 14 of the non-conductive member 12 such that at least a portion of the first opposite planar side 14 is exposed near the sharp cutting edge 26. Ultrapolar electrosurgery blade 10 also includes conductive insert members 80 that are in communication with active and return electrodes contained on the non-conductive member. FIG. 7 shows the active electrode 30 on first opposite planar side 14 in communication with one of the conductive insert members 80 thereby making that conductive insert member a top active conductive insert member. Active electrode 30 may be a conductive layer that is deposited on the first opposite planar side 14 of the non-conductive member 12 and may comprise stainless steel, copper, and/or tungsten. As shown in FIG. 7, active electrode 30 is an elongated conductive layer that extends along a length of the first opposite planar side 14 of the non-conductive member 12 near the top 18 of the non-conductive member 12 with a "V" shaped hook like shape that is positioned on the first opposite planar side 14 of the non-conductive member 12 near the cutting end 22 of the non-conductive member 12. The active electrode 30 also extends along an entire length of the first opposite planar side 14 of the non-conductive member 12 to the non-cutting end 24 of the non-conductive member 12 and then wraps around the non-cutting end 24 of non-conductive member 12 so that active electrode 30 is in communication with one of conductive insert members 80. Non-conductive member 12 also includes openings (not shown) within the non-cutting end 24 for insertion of conductive insert members 80 and a rounded portion 94 which lies adjacent to an inner circumference of an electrosurgery pencil when the ultrapolar electrosurgery blade 10 is positioned within an electrosurgery.

Figure 8:
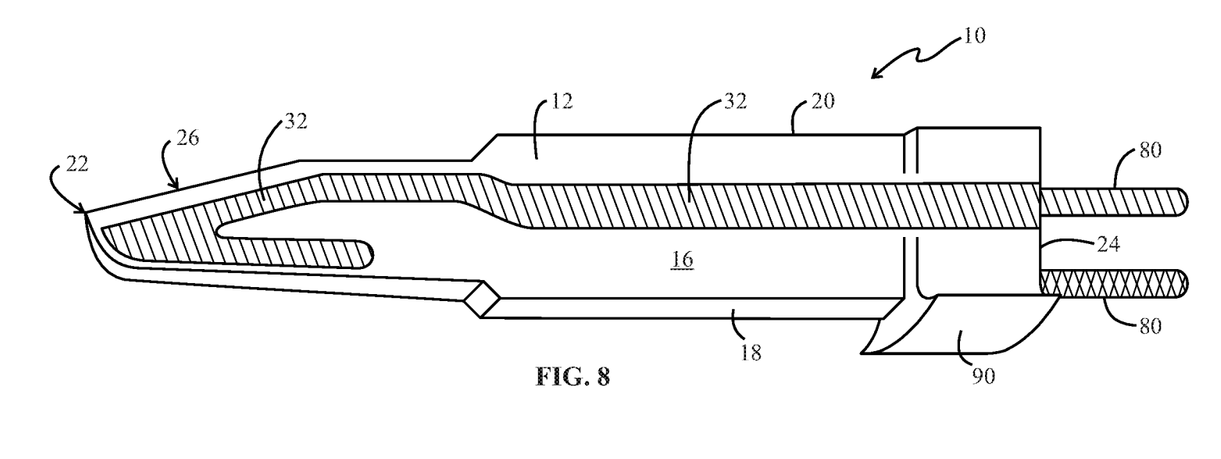
FIG. 8 is an opposite side view of the exemplary embodiment of the ultrapolar electrosurgery blade shown in FIG. 7.

FIG. 8 is an opposite side view of the exemplary embodiment of the ultrapolar electrosurgery blade 10 shown in FIG. 7. Ultrapolar electrosurgery blade 10 includes non-conductive member 12 having first and second opposite planar sides 14, 16, a top 18, a bottom 20, a cutting end a sharp cutting edge 26, and a non-cutting end 24, and a return electrode 32 positioned on the second opposite planar side 16 of the non-conductive member 12 such that at least a portion of the second opposite planar side 16 is exposed near the sharp cutting edge 26. Ultrapolar electrosurgery blade 10 also includes conductive insert members 80 that are in communication with active and return electrodes contained on the non-conductive ember 12. FIG. 8 shows the return electrode 32 on second opposite planar side 16 in communication with one of the conductive insert members 80 thereby making that conductive insert member a bottom return conductive insert member. Return electrode 32 may be a conductive layer that is deposited on the second opposite planar side 16 of the non-conductive member 12 and may comprise stainless steel, copper, and/or tungsten. As shown in FIG. 8, return electrode 32 is an elongated conductive layer that extends along a length of the second opposite planar side 16 of the non-conductive member 12 near the top 18 of the non-conductive member 12 with a "V" shaped book like shape that is positioned on the second opposite planar side 16 of the non-conductive member 12 near the cutting end 22 of the non-conductive member 12. The return electrode 32 also extends along an entire length of the second opposite planar side 16 of the non-conductive member 12 to the non-cutting end 24 of the non-conductive member 12 and then wraps around the non-cutting end 24 of non-conductive member 12 so that return electrode 32 is in communication with one of conductive insert members 80. Non-conductive member 12 also includes openings (not shown) within the non-cutting end 24 for insertion of conductive insert members 80 and a rounded portion 94 which lies adjacent to an inner circumference of an electrosurgery pencil when the ultrapolar electrosurgery blade 10 is positioned within an electrosurgery pencil. Active electrode 30 and return electrode 32 located on first and second opposite planar sides 14, 16 of non-conductive member 12, respectively, are opposing mirror images of one another.

Figure 9:
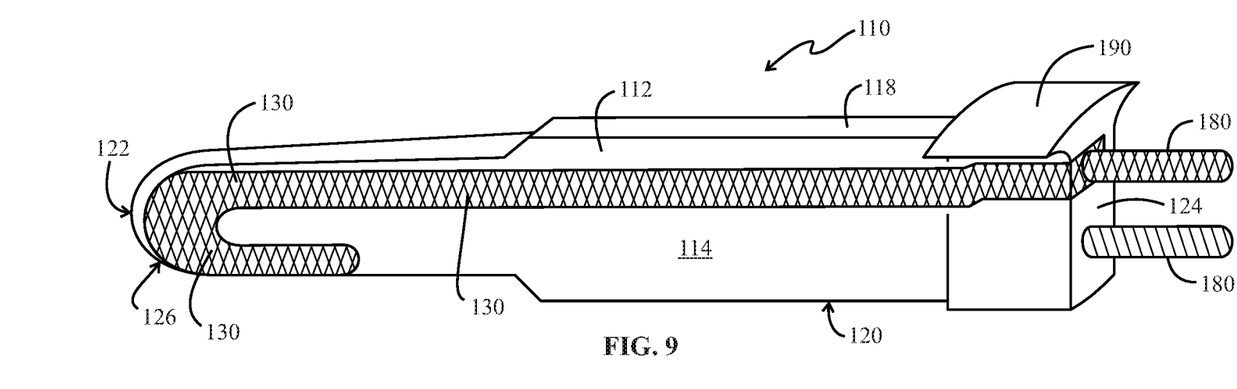
FIG. 9 is a side perspective view of another exemplary embodiment of the ultrapolar electrosurgery blade of the present invention.

FIG. 9 is a side perspective view of another exemplary embodiment of the ultrapolar electrosurgery blade 100 of the present invention which includes non-conductive member 112 having first and second opposite planar sides 114, 116, a top 118, a bottom 120, a cutting end 122 with a sharp cutting edge 126, and a non-cutting end 124, and an active electrode 130 positioned on the first opposite planar side 114 of the non-conductive member 112 such that at least a portion of the first opposite planar side 114 is exposed near the sharp cutting edge 126. Ultrapolar electrosurgery blade 110 also includes conductive insert members 180 that are in communication with active and return electrodes contained on the non-conductive member. FIG. 9 shows the active electrode 130 on first opposite planar side 114 in communication with one of the conductive insert members 180 thereby making that conductive insert member a top active conductive insert member. Active electrode 130 may be a conductive layer that is deposited on the first opposite planar side 114 of the non-conductive member 112 and may comprise stainless steel, copper, and/or tungsten. As shown in FIG. 9, active electrode 130 is an elongated conductive layer that extends along a length of the first opposite planar side 114 of the non-conductive member 12 near the top 118 of the non-conductive member 112 with a "U" shaped hook like shape that is positioned on the first opposite planar side 114 of the non-conductive member 112 near the cutting end 122 of the non-conductive member 112. The "U" hook like shape of the active electrode 130 extends to the bottom 118 of the non-conductive member 112 but does not extend all the way to the cutting end 122 so that a portion of the first opposite planar side 114 of the non-conductive member 112 is exposed between active electrode 130 and the cutting end 122. Active electrode 130 also extends along an entire length of the first opposite planar side 114 of the non-conductive member 112 to the non-cutting end 124 of the non-conductive member 112 and then wraps around the non-cutting end 124 of non-conductive member 112 so that active electrode 130 is in communication with one of conductive insert members 180. Non-conductive member 112 also includes openings (not shown) within the non-cutting end 124 for insertion of conductive insert members 180 and a rounded portion 194 which lies adjacent to an Inner circumference of an electrosurgery pencil when the ultrapolar electrosurgery blade 110 is positioned within an electrosurgery pencil.

Figure 10:
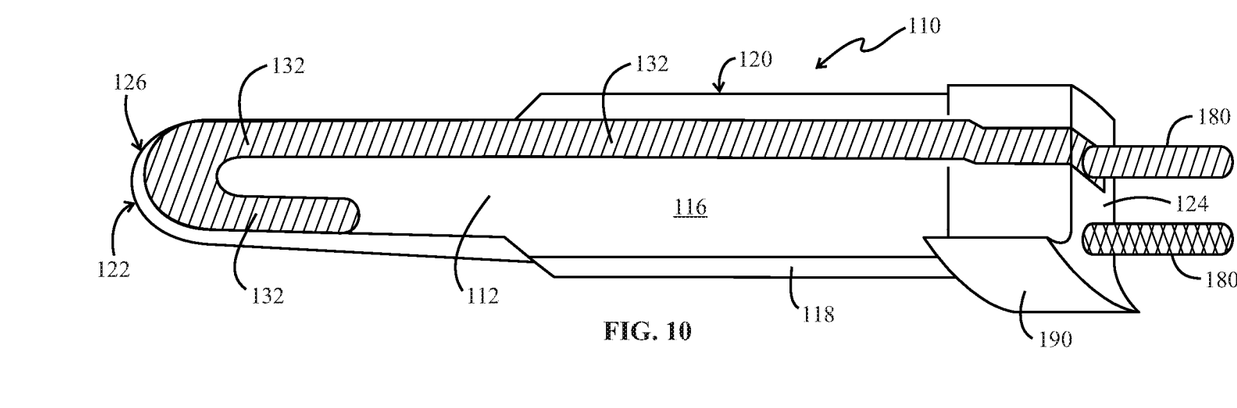
FIG. 10 is an opposite side view of the exemplary embodiment of the ultrapolar electrosurgery blade shown in FIG. 9.

FIG. 10 is an opposite side view of the exemplary embodiment of the ultrapolar electrosurgery blade 110 shown in FIG. 9. Ultrapolar electrosurgery blade 110 includes non-conductive member 112 having first and second opposite planar sides 114, 116, a top 118, a bottom 120, a cutting end 122 with a sharp cutting edge 126, and a non-cutting end 124, and a return electrode 132 positioned on the second opposite planar side 116 of the non-conductive member 112 such that at least a portion of the second opposite planar side 116 is exposed near the sharp cutting edge 126. Ultrapolar electrosurgery blade 110 also includes conductive insert members 180 that are in communication with active and return electrodes contained on the non-conductive member 112. FIG. 10 shows the return electrode 132 on second opposite planar side 116 in communication with one of the conductive insert members 180 thereby making that conductive insert member a bottom return conductive insert member. Return electrode 132 may be a conductive layer that is deposited on the second opposite planar side 116 of the non-conductive member 112 and may comprise stainless steel, copper, and/or tungsten. As shown in FIG. 10, return electrode 132 is an elongated conductive layer that extends along a length of the second Opposite planar side 116 of the non-conductive member 112 near the top 118 of the non-conductive member 112 with a "U" shaped hook like shape that is positioned on the second opposite planar side 116 of the non-conductive member 112 near the cutting end 122 of the non-conductive member 112. The "U" hook like shape of the return electrode 112 extends to the bottom 120 of the non-conductive member 112 but does not extend all the way to the cutting end 122 so that a portion of the second opposite planar side 116 of the non-conductive member 112 is exposed between return electrode 132 and the cutting end 122. The return electrode 132 also extends along an entire length of the second opposite planar side 116 of the non-conductive member 112 to the non-cutting end 124 of the non-conductive member 112 and then wraps around the non-cutting end 124 of non-conductive member 112 so that return electrode 132 is in communication with one of conductive insert members 180. Non-conductive member 112 also includes openings (not shown) within the non-cutting end 124 for insertion of conductive insert members 180 and a rounded portion 194 which lies adjacent to an inner circumference of an electrosurgery pencil when the ultrapolar electrosurgery blade 110 is positioned within an electrosurgery pencil. Active electrode 130 and return electrode 132 located on first and second opposite planar sides 114, 116 of non-conductive member 112, respectively, are opposing mirror images of one another.

Figure 11:
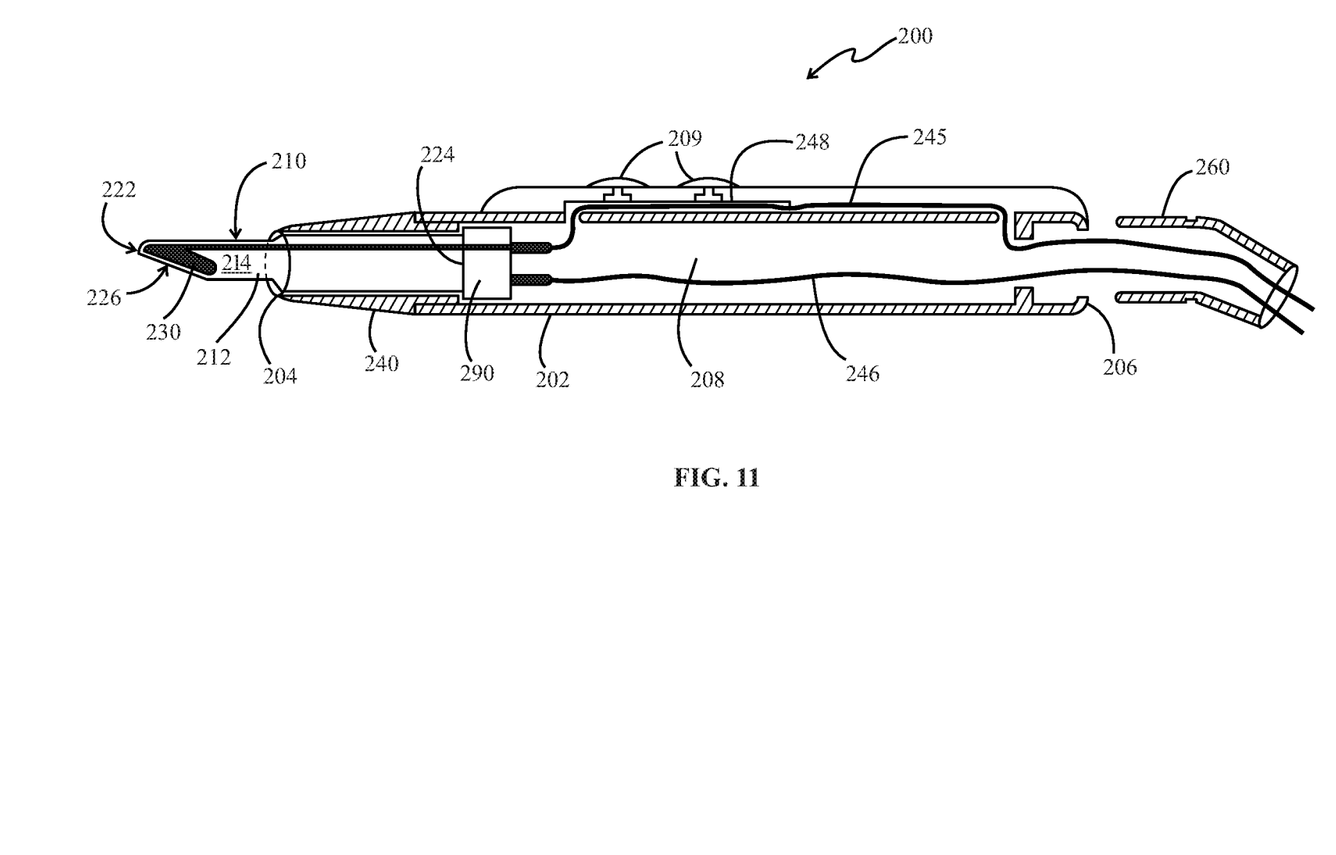
FIG. 11 is a side cross-sectional view of an exemplary embodiment of ultrapolar electrosurgery pencil of the present invention.

FIG. 11 is a side cross-sectional view of an exemplary embodiment of an ultrapolar electrosurgery pencil 200 of the present invention. The ultrapolar electrosurgery pencil 200 includes a handpiece 202 with a first and second end 204, 206 and an electrosurgery blade 210 positioned in the first end 204 of the handpiece 202 where the electrosurgery blade 210 includes a non-conductive planar member 212 having opposing planar sides 214, 216, a cutting end 222 with a sharp cutting, edge 226, and an opposite non-cutting end 224, an active electrode 230 located on one opposing planar side 214 where at least a portion of the opposing planar side 214 is exposed near the non-conductive cutting end 222 of the non-conductive planar member 212, and a return electrode 232 (not shown as it is on opposite side) located on the other opposing planar side 216 (not shown) where at least a portion of the other opposing planar side is exposed near the non-conductive cutting end 222 of the non-conductive planar member 212. The handpiece 202 may further comprise a smoke evacuation channel 208 contained therein for evacuating smoke and debris from the surgical site during activation of the electrosurgery pencil 200. In addition, die handpiece 202 may further comprise only one activation button 209 for coagulation since the sharp cutting edge 226 of the nonconductive planar member 212 can make precise cuts without having power applied to the ultrapolar electrosurgery blade 210. Alternatively, the handpiece 202 may include more than one activation button for cutting and coagulation. The ultrapolar electrosurgery blade 210 may also include a connector 290 which functions to connect the ultrapolar electrosurgery blade 210 to an electrosurgery pencil. The ultrapolar electrosurgery pencil 200 may also include a nozzle member 240, which may be transparent, connected to the handpiece 202 where the first end 204 of the handpiece 202 is then part of the nozzle member 240. The ultrapolar electrosurgery handpiece 200 also includes a conductive communication means, such as a wire 245, for connecting the active electrode 230 of the ultrapolar electrosurgery blade 210 to a circuit board 248 of the ultrapolar electrosurgery pencil 200 and a conductive communication means, such as wire 246, for connecting return electrode 232 of the ultrapolar electrosurgery blade 210 to a power cord (not shown) which contains the conductive wiring for the ultrapolar electrosurgery pencil 200. The ultrapolar electrosurgery pencil 200 may also include a swivel member 260 connected to the second end 206 of the handpiece 202 which is in turn connected to a vacuum tube for evacuating smoke and debris from the surgical site.

Unique Features and Advantages of the Ultrapolar Electrosurgery Blade and Pencil The top of the non-conductive member of the ultrapolar electrosurgery blade can be wider than the sharp cutting end and sharp cutting edge of the ultrapolar electrosurgery blade located on the bottom of the non-conductive planar member (as can be seen in FIGS. 1-3 and 7-8).

The conductive layers that make up the active and return electrodes located on opposing sides of the non-conductive member of the ultrapolar electrosurgery blade may take on any number of configurations while still enabling the electrosurgery blade to function at very low power levels (such as 15-20 Watts or even less) while cutting and coagulating tissue. The ultrapolar electrosurgery blade and pencil of the present invention can operate and function using low power because the tissue resistance is greatly reduced by not having current go through the patient's body. Unlike other electrosurgery pencils, the ultrapolar electrosurgery blade and pencil of the present invention do not require the placement of a return electrode pad on the patient's body. As a result, no radio frequency current is passing through the patient's body so the body resistance is almost zero. In addition, the present invention is much safer that other electrosurgery pencils because the patient is not at risk of being burned by the return electrode since no return electrode is placed on the patient and no current is passing through the body of the patient.

The sharp cutting edge of the ultrapolar electrosurgery blade can rut tissue without applying power to the ultrapolar electrosurgery blade and can also cut and coagulate tissue when power is applied to the ultrapolar electrosurgery blade.

The ultrapolar electrosurgery blade and pencil stop tissue from bleeding after cutting with minimal or no lateral damage to the tissue and without charring or burning of the tissue. Further, tissue does not stick to the ultrapolar electrosurgery blade while cutting and/or coagulating tissue. In addition, very little smoke is produced when using the ultrapolar electrosurgery blade and pencil due to the low or reduced power required for the ultrapolar electrosurgery blade to function and the minimal or non-existent charring of tissue.

The ultrapolar electrosurgery blade and pencil of the present invention can be used in both monopolar and bipolar modes thereby Providing an electrosurgery blade that can be used with almost any electrosurgery pencil and an electrosurgery pencil that be used with almost any electrosurgical unit.

The above exemplary embodiments are not intended to limit the scope, applicability, or configuration of the invention in any way. Rather, the disclosure is intended to teach both the implementation of the exemplary embodiments and modes and any equivalent modes or embodiments that are known or obvious to those reasonably skilled in the art. Additionally, all included figures are non-limiting illustrations of the exemplary embodiments and modes, which similarly avail themselves to any equivalent modes or embodiments that are known or obvious to those reasonably skilled in the art.

Other combinations and/or modifications of structures, arrangements, applications, proportions, elements, materials, or components used in the practice of the instant invention, in addition to those not specifically recited, can be varied or otherwise particularly adapted to specific environments, manufacturing specifications, design parameters, or other operating requirements without departing from the scope of the instant invention and are intended to be included in this disclosure.

The invention claimed is:

1. An electrosurgery blade comprising:
a non-conductive member having a first and second opposite planar sides and a sharp cutting end;
an active electrode having a straight elongated portion extending from a shortened curved or angular hook portion positioned on the first opposite planar side of the non-conductive member such that at least a portion of the first opposite planar side is exposed between the shortened curved or angular hook portion of the active electrode and the sharp cutting end; and
a return electrode positioned on the second opposite planar side of the non-conductive member such that at least a portion of the second opposite planar side is exposed between the return electrode and the sharp cutting end.

2. The electrosurgery blade of claim 1 wherein the active and return electrodes comprise opposing mirror images of one another.

3. The electrosurgery blade of claim 1 wherein the non-conductive member comprises a ceramic.

4. The electrosurgery blade of claim 1 wherein the active and return electrodes each comprise at least one of a stainless steel, a copper, and a tungsten.

5. The electrosurgery blade of claim 1 wherein the non-conductive member further comprises a non-cutting end located opposite the cutting end wherein the active and return electrodes each extend to the non-cutting end of the non-conductive member.

6. The electrosurgery Glade of claim 5 further comprising first and second conductive insert members connected to the non-cutting end of the non-conductive member such that the first conductive insert member is in communication with the active electrode and the second conductive insert member is in communication with the return electrode.

7. The electrosurgery blade of claim 1 wherein the electrosurgery blade can be used in both a monopolar and a bipolar mode when used to perform electrosurgery.

8. An electrosurgery handpiece pencil comprising:
a handpiece member; and
an electrosurgery blade connected to the handpiece wherein the electrosurgery blade comprises a non-conductive member having opposing planar sides and a sharp cutting end, an active electrode having a straight elongated portion extending from a shortened curved or angular hook portion on one opposing planar side of the non-conductive member such that at least a portion of the opposing planar side is exposed between the shortened curved or angular hook portion of the active electrode and the sharp cutting end, and a return electrode on the other opposing planar side of the non-conductive member such that at least a portion of the other opposing planar side is exposed near the sharp cutting end.

9. The electrosurgery handpiece pencil of claim 8 wherein the handpiece member has only one activation button and that activation button is for coagulation.

* * * * *